United States Patent
Bayach et al.

(10) Patent No.: US 11,897,855 B1
(45) Date of Patent: *Feb. 13, 2024

(54) ANTIOXIDANT VITAMIN C DERIVATIVE

(71) Applicant: KING FAISAL UNIVERSITY, Al-Ahsa (SA)

(72) Inventors: Imene Bayach, Al-Ahsa (SA); Amel Ibrahim, Al-Ahsa (SA); Nadeem Sadiq Sheikh, Al-Ahsa (SA); Khurshid Ayub, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/220,739

(22) Filed: Jul. 11, 2023

(51) Int. Cl.
  *C07D 307/33* (2006.01)
  *A61Q 19/08* (2006.01)
  *A61K 8/49* (2006.01)

(52) U.S. Cl.
  CPC .......... *C07D 307/33* (2013.01); *A61K 8/4973* (2013.01); *A61Q 19/08* (2013.01)

(58) Field of Classification Search
  CPC .................................................. C07D 307/33
  See application file for complete search history.

(56) References Cited

U.S. PATENT DOCUMENTS

2010/0159471 A1   6/2010   Taniuchi et al.

OTHER PUBLICATIONS

Andrijana Meš ci' c Macan, et al., "Therapeutic Perspective of Vitamin C and Its Derivatives"; Antioxidants (Basel). Aug. 2019; 8(8): 247. Published online Jul. 2, 20196. doi: 10.3390/antiox8080247.

Peng He, et al., "Ascorbic acid analogue 6-Deoxy-6-[ 18 F] fluoro-L-ascorbic acid as a tracer for identifying human colorectal cancer with SVCT2 overexpression"; Transl Oncol. May 2021; 14(5):101055. doi: 10.1016/j.tranon.2021.101055. Epub Mar. 4, 2021.

Makoto Satake, et al., Vitamin C Metabolomic Mapping in the Lens with 6-Deoxy-6-fluoro-ascorbic Acid and High-Resolution 19F-NMR Spectroscopy.

*Primary Examiner* — Golam M Shameem
(74) *Attorney, Agent, or Firm* — Nath, Goldberg & Meyer; Richard C. Litman

(57) ABSTRACT

A structural modification of vitamin C designed to increase its antioxidant activity is provided. The approach involves the substitution of the hydroxyl group (OH) by fluorine (F) at position 4 of vitamin C, resulting in the formation of a new structure. Based on quantum calculations, this modification may enhance the antioxidant properties of vitamin C and its ability to scavenge free radicals.

10 Claims, No Drawings

ANTIOXIDANT VITAMIN C DERIVATIVE

BACKGROUND

1. Field

The present disclosure relates to a new antioxidant molecule, a vitamin C derivative that may enhance the antioxidant properties of vitamin C and its ability to scavenge free radicals.

2. Description of the Related Art

Vitamin C, also known as ascorbic acid, is an essential water-soluble vitamin that plays a crucial role in various biological processes. It is required for the synthesis of collagen, a structural protein that provides strength and elasticity to tissues such as skin, cartilage, and bone. Vitamin C also acts as a powerful antioxidant, neutralizing harmful free radicals and protecting cells from oxidative damage. Vitamin C deficiency can lead to scurvy, a condition characterized by fatigue, weakness, bleeding gums, and skin lesions. While scurvy is now rare in developed countries, suboptimal vitamin C intake is still common and may contribute to a variety of health problems, including impaired immune function, poor wound healing, and an increased risk of chronic diseases such as cardiovascular disease and certain cancers.

Vitamin C is a biomolecule of critical importance for protection of cellular components against oxidative damage caused by toxic free radicals and other reactive oxygen species (ROS) that are involved in the development of various types of chronic diseases. Vitamin C has a switchover role from being an antioxidant in physiological conditions to a prooxidant under pathologic conditions. Moreover, some L-ascorbic acid derivatives exhibit strong and selective antitumor and antiviral activity.

Vitamin C is an essential, water-soluble micronutrient that exists predominantly as the ascorbate anion under physiological pH conditions, arising from the completely dissociated 3-hydroxyl group. ASA contains a lactone ring with an electron rich 2-en-2,3-diol-1-one moiety. As a reducing agent and electron donor antioxidant, ASA can undergo two consecutive one-electron oxidation reactions and deprotonation of both hydroxyl groups at positions 2 and 3, resulting in the formation of dehydroascorbic acid.

The hydroxyl group at position 3, as a vinylogous carboxylic acid, ionizes first, and ASA is ionized at physiological pH to its highly polar, water-soluble 3-monoanion. At pH 7, 99.9% of vitamin C is present as the anion, therefore the antioxidant chemistry of vitamin C is the chemistry of the anion. Loss of one electron gives an ascorbate radical, which is resonance stabilized. Because of the low reduction potential of the ascorbate radical/ascorbate couple ($E^0=282$ mV), almost every oxidizing radical formed in the biological system causes one electron oxidation, resulting in the ascorbate radical. The ionization of the 2-OH group is more facile than the ionization of the 2-OH group of the monoanion. In this process, ASA donates two protons and two electrons to terminate the radical chain reactions. Dehydroascorbic acid forms a hydrate that cyclizes to the bicyclic hemiacetal, which is structurally similar to glucose and, therefore, is transported to cells by glucose transporters (GLUTs).

ASA is taken up by most cell types via a high affinity/low capacity mechanism through sodium-dependent vitamin C transporter (SVCT-1 and 2), or as dehydroascorbic acid (DHA) being accumulated via sodium-independent facilitative GLUTs, followed by intracellular reduction. While the reduced form of ascorbate is dominant in the plasma of healthy humans, DHA is present at a very low level, indicating that ascorbate is taken up and accumulated in cells primarily by SVCTs.

In the early 1970s, the two-time Nobel Prize-winning chemist Linus Pauling reported that high doses of vitamin C reduced cancer by acting as an antioxidant. L. Pauling and E. Cameron demonstrated that intravenous administration of vitamin C, followed by oral use, led to an increased rate of survival of cancer patients. On the contrary, other clinical studies have shown that vitamin C has a low antitumor effect. Further, these effects have not been seen by other antioxidants, including certain vitamin C derivatives.

Structural modification of vitamin C has been extensively studied due to its potential to improve the stability, bioavailability, and physiological effects of the compound. These structural modifications of vitamin C hold promise for improving its therapeutic potential and addressing its limitations, such as its instability and low bioavailability.

Thus, the development of new antioxidants, and particularly to new vitamin C derivatives, solving the aforementioned problems are desired.

SUMMARY

The present subject matter relates to the structural modification of vitamin C to increase its antioxidant activity. The approach involves the substitution of the hydroxyl group (OH) by fluorine (F) at position 4 of vitamin C, resulting in the formation of a new structure. Based on quantum calculations, this modification may enhance the antioxidant properties of vitamin C and its ability to scavenge free radicals.

In an embodiment, the present subject matter relates to a vitamin C derivative compound having the formula:

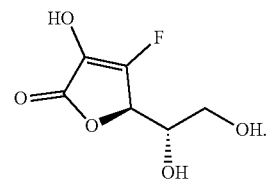 [SMILES: O=C1O[C@H]([C@@H](O)CO)C(F)=C1O]

In another embodiment, the present subject matter relates to a pharmaceutical composition, comprising the vitamin C derivative compound and a pharmaceutically acceptable carrier.

In a further embodiment, the present subject matter relates to a cosmetic composition, comprising the vitamin C derivative compound and a cosmetically acceptable carrier.

In additional embodiments, the present subject matter relates to methods of promoting an antioxidant activity in a subject, promoting skin health in a subject, and/or protecting skin against oxidative damage in a subject, the methods comprising administering to a subject in need thereof the pharmaceutical composition and/or the cosmetic composition as described herein.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a disorder or disease having an oxidative component.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a vitamin C derivative compound having the formula:

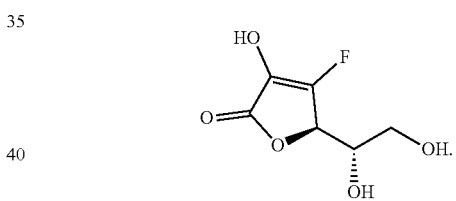

In this regard, the present vitamin C derivative involves the substitution of the hydroxy group at position 4 of the five-membered ring with a fluorine, resulting in the formation of a new structure (or derivative):

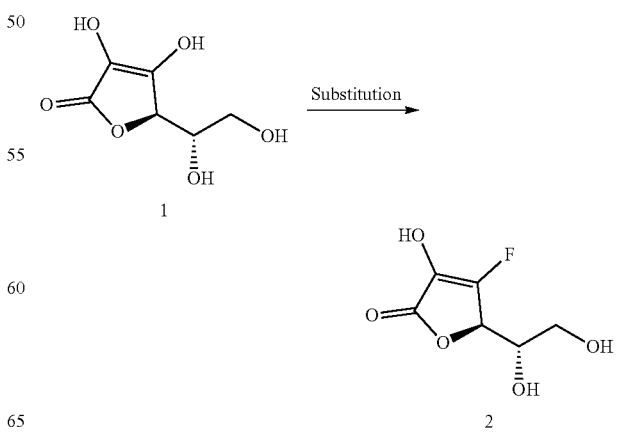

Density Functional Theory (DFT) calculations were performed to determine the BDE values for vitamin C and the 3F and 4F substituted derivatives thereof. Such DFT calculations are well known in the art to be accurate in predicting antioxidant activity of compounds. Table 1 below shows the calculated Bond Dissociation Enthalpies (BDEs) in kcal/mol for vitamin C, its 3F derivative, and the present 4F derivative using B3LYP/31+G(d,p).

TABLE 1

| Name | Structure | BDE (3OH) | BDE (4OH) |
|---|---|---|---|
| Vit. C | 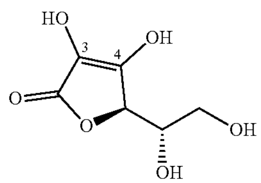 [SMILES: O=C1O[C@H]([C@@H](O)CO)C(O)=C1O] | 88.2 | 80.9 |
| 3F-Vit. C | 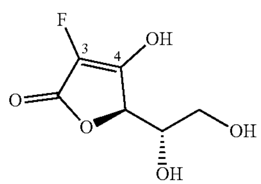 [SMILES: O=C1O[C@H]([C@@H](O)CO)C(O)=C1F] | — | 80.4 |
| 4F-Vit. C | 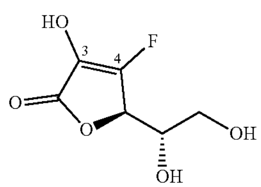 [SMILES: O=C1O[C@H]([C@@H](O)CO)C(F)=C1O] | 87.0 | — |

Based on the results shown in Table 1, the present compound, 4F-vitamin C, has a lower BDE in the 3OH position than vitamin C, indicating superior antioxidant activity. Further the decrease in the BDE at the 3OH position for 4F-vitamin C is greater than the decrease in the BDE at the 4OH position for 3F-vitamin C, indicating the present 4F-vitamin C has superior antioxidant activity to 3F-vitamin C. Accordingly, the presently modified 4F-vitamin C derivative can enhance the antioxidant properties of vitamin C and its ability to scavenge free radicals.

Accordingly, in an embodiment, the vitamin C derivative compound has a bond dissociation enthalpy (BDE) of about 87 kcal/mol.

In another embodiment, the present subject matter relates to a pharmaceutical composition, comprising the vitamin C derivative compound and a pharmaceutically acceptable carrier.

In a further embodiment, the present subject matter relates to a cosmetic composition, comprising the vitamin C derivative compound and a cosmetically acceptable carrier.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound would typically be administered at a therapeutically or pharmaceutically effective dosage, or at a cosmetically acceptable dosage, which would be expected to be lower than the therapeutically or pharmaceutically effective dosage. Administration of the compounds or compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics/cosmetics or combination of therapeutics/cosmetics selected for administration. The subject may be administered as many doses as is required to reduce and/or alleviate the signs, symptoms, or causes of the disease or disorder in question, or bring about any other desired alteration of a biological system.

In employing the present compound, any pharmaceutically or cosmetically acceptable mode of administration can be used with other acceptable excipients, including solid, semi-solid, liquid or aerosol dosage forms, such as, for example, tablets, capsules, powders, liquids, suspensions, suppositories, aerosols or the like. In an embodiment, the dosage form is likely to be a topical dosage form, such as a cream, lotion, ointment, gel, foam, aerosol, or the like. In such an embodiment, the topical dosage form is likely to be applied to an area of a patient's skin to be treated.

In additional embodiments, the present subject matter relates to methods of promoting an antioxidant activity in a subject, promoting skin health in a subject, and/or protecting skin against oxidative damage in a subject, the methods comprising administering to a subject in need thereof the pharmaceutical composition and/or the cosmetic composition as described herein.

Generally, depending on the intended mode of administration, the composition will contain about 0.1% to 90%, for example about 0.5% to 50%, by weight of the present compound, the remainder being suitable excipients, carriers, etc.

The present compound is expected to have valuable pharmaceutical and cosmetic properties, which makes it commercially utilizable. Accordingly, the present subject matter further relates to use of the present compound for the treatment of diseases, disorders, or conditions having oxidative activity.

It is to be understood that the vitamin C derivative compound is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A vitamin C derivative compound having the formula:

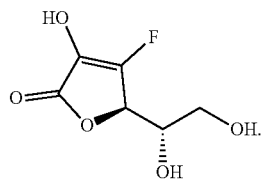 [SMILES: O=C1O[C@H]([C@@H](O)CO)C(F)=C1O]

2. The vitamin C derivative compound of claim 1, having a bond dissociation enthalpy (BDE) of about 87 kcal/mol.

3. A pharmaceutical composition, comprising the vitamin C derivative compound of claim 1 and a pharmaceutically acceptable carrier.

4. A cosmetic composition, comprising the vitamin C derivative compound of claim 1 and a cosmetically acceptable carrier.

5. A method of promoting an antioxidant activity in a subject, the method comprising administering to a subject in need thereof the pharmaceutical composition of claim 3.

6. A method of promoting an antioxidant activity in a subject, the method comprising administering to a subject in need thereof the cosmetic composition of claim 4.

7. A method of promoting skin health in a subject, the method comprising administering to a subject in need thereof the pharmaceutical composition of claim 3.

8. A method of promoting skin health in a subject, the method comprising administering to a subject in need thereof the cosmetic composition of claim 4.

9. A method of protecting skin against oxidative damage in a subject, the method comprising administering to a subject in need thereof the pharmaceutical composition of claim 3.

10. A method of protecting skin against oxidative damage in a subject, the method comprising administering to a subject in need thereof the cosmetic composition of claim 4.

* * * * *